(12) United States Patent
Bernal et al.

(10) Patent No.: US 9,226,691 B2
(45) Date of Patent: *Jan. 5, 2016

(54) PROCESSING A VIDEO FOR TIDAL CHEST VOLUME ESTIMATION

(75) Inventors: Edgar A. Bernal, Webster, NY (US); Lalit Keshav Mestha, Fairport, NY (US); Beilei Xu, Penfield, NY (US)

(73) Assignee: Xerox Corporation, Norwalk, CT (US)

( * ) Notice: Subject to any disclaimer, the term of this patent is extended or adjusted under 35 U.S.C. 154(b) by 538 days.

This patent is subject to a terminal disclaimer.

(21) Appl. No.: 13/486,637

(22) Filed: Jun. 1, 2012

(65) Prior Publication Data

US 2013/0324876 A1     Dec. 5, 2013

(51) Int. Cl.
| | |
|---|---|
| *A61B 5/091* | (2006.01) |
| *A61B 5/00* | (2006.01) |
| *A61B 5/107* | (2006.01) |
| *A61B 5/11* | (2006.01) |
| *A61B 5/113* | (2006.01) |
| *G01B 11/25* | (2006.01) |

(52) U.S. Cl.
CPC ............... *A61B 5/091* (2013.01); *A61B 5/0064* (2013.01); *A61B 5/1077* (2013.01); *A61B 5/1128* (2013.01); *A61B 5/1135* (2013.01); *G01B 11/2527* (2013.01)

(58) Field of Classification Search
USPC .................................. 600/411, 376, 427, 407
See application file for complete search history.

(56) References Cited

U.S. PATENT DOCUMENTS

| | | |
|---|---|---|
| 5,107,845 A | 4/1992 | Guern et al. |
| 5,800,360 A | 9/1998 | Kisner et al. |
| 6,920,236 B2 | 7/2005 | Prokoski |
| 6,958,809 B2 | 10/2005 | Sterling et al. |
| 6,989,891 B2 | 1/2006 | Braig et al. |
| 7,050,157 B2 | 5/2006 | Braig et al. |
| 7,061,593 B2 | 6/2006 | Braig et al. |
| 7,436,510 B2 | 10/2008 | Grun et al. |
| 7,480,032 B2 | 1/2009 | Braig et al. |
| 7,570,979 B2 | 8/2009 | Cooper |
| 7,729,750 B2 | 6/2010 | Tromberg et al. |
| 7,738,085 B2 | 6/2010 | Braig et al. |

(Continued)

OTHER PUBLICATIONS

Morgan et al (Contribution of the rib cage to breathing in tetraplegia, Torax 1985: 40: 613-617).*

(Continued)

*Primary Examiner* — Joel F Brutus
(74) *Attorney, Agent, or Firm* — Philip E. Blair; Fleit Gibbons Gutman Bongini & Bianco P.L.

(57) ABSTRACT

What is disclosed is a system and method for estimating tidal chest volume using 3D surface reconstruction based on an analysis of captured reflections of structured illumination patterns from the subject with a video camera. The imaging system hereof captures the reflection of the light patterns from a target area of the subject's thoracic region. The captured information produces a depth map and a volume is estimated from the resulting 3D map. The teachings hereof provide a non-contact approach to patient respiration monitoring that is particularly useful for infant care in a neo-natal intensive care unit (NICU), and can aid in the early detection of sudden deterioration of physiological condition due to detectable changes in respiratory function. The systems and methods disclosed herein provide an effective tool for tidal chest volume study and respiratory function analysis.

19 Claims, 11 Drawing Sheets

(56) References Cited

U.S. PATENT DOCUMENTS

| | | | |
|---|---|---|---|
| 7,760,354 | B2 | 7/2010 | Grun et al. |
| 7,872,734 | B2 | 1/2011 | Braig et al. |
| 7,896,498 | B2 | 3/2011 | Munger et al. |
| 7,899,764 | B2 | 3/2011 | Martin et al. |
| 2009/0275808 | A1 | 11/2009 | DiMaio et al. |
| 2009/0318815 | A1 | 12/2009 | Barnes et al. |
| 2010/0249630 | A1 | 9/2010 | Droitcour et al. |
| 2010/0284082 | A1 | 11/2010 | Shpunt et al. |

OTHER PUBLICATIONS

Binks et al (An inexpensive, MRI compatible device to measure tidal volume from chest-wII circumference, 2007).*

Chung et al (Fractal analysis of nuclear medicine images for the diagnosis of pulmonary emphysema, Apr. 2000).*

Mestha et al., "3D Imaging Using Structured Light for Accurate Vehicle Occupancy Determination", U.S. Appl. No. 13/476,334, filed May 21, 2012.

Mestha et al., "Processing a Video for Vascular Pattern Detection and Cardiac Function Analysis", U.S. Appl. No. 13/483,992, filed May 30, 2012.

Xu et al., "Eliminating Artifacts From a Video of a Scene Illuminated With Unstructured and Structured Illumination Sources", U.S. Appl. No. 13/533,605, filed Jun. 26, 2012.

Wang et al., "Multi-Band Infrared Camera System Optimized for Skin Detection", U.S. Appl. No. 13/416,436, filed Mar. 9, 2012.

Xu et al., "Monitoring Respiration With a Thermal Imaging System", U.S. Appl. No. 13/103,406, filed May 9, 2011.

Cardoso et al., "Minimally Invasive Image-Based Determination of Carbon Dioxide (CO2) Concentration in Exhaled Breath", U.S. Appl. No. 13/246,560, filed Sep. 27, 2011.

Piratla et al., "Web-Based System and Method for Video Analysis", U.S. Appl. No. 13/417,979, filed Mar. 12, 2012.

Mestha et al., "Filtering Source Video Data Via Independent Component Selection", U.S. Appl. No. 13/281,975, filed Oct. 26, 2011.

Mestha et al., "Removing Environment Factors From Signals Generated From Video Images Captured for Biomedical Measurements", U.S. Appl. No. 13/401,207, filed Feb. 21, 2012.

Geng, Jason "Structured-Light 3D Surface Imaging: A Tutorial", by Jason Geng, Advances in Optics and Photonics vol. 3, pp. 128-160, Optical Society of America, Mar. 31, 2011.

Quan et al., "Shape measurement of small objects using LCD fringe projection with phase shifting," Optics Communications, vol. 189, pp. 21-29, 2001.

Groote et al., "Measurement of thoracoabdominal asynchrony: importance of sensor sensitivity to cross-section deformations," J. Appl. Physiol. 88, 1295-1302 (2000).

Levine et al., "Use of a triaxial magnetometer for respiratory measurements," J. Appl. Physiol. 70, 2311-2321(1991).

Allsop et al., "Application of long-period grating sensors to respiratory plethysmography," J. Biomed. Opt. 12, 064003 (2007).

Babchenko et al., "Fiber optic sensor for the measurement of respiratory chest circumference changes," J. Biomed. Opt. 4, 224-229 (1999).

Aliverti et al., "Optoelectronic plethysmography in intensive care patients," Am J Respir Crit Care Med 161, 1546-1552 (2000).

Saumarez, R.C., "Automated optical measurements of human torso surface movements during breathing," J. Appl. Physiol. 60, 702-709 (1986).

Ferrigno et al., "Three-dimensional optical analysis of chest wall motion," J. Appl. Physiol. 77, 1224-1231 (1994).

Aliverti et al., "Compartmental analysis of breathing in the supine and prone position by optoelectronic plethysmography," Ann. Biomed. Eng. 29, 60-70 (2004).

Chen et al., "Color structured light system of chest wall motion measurement for respiratory volume evaluation", J. Biomed. Opt. 15, 026013 (2010).

Drummond et al., "A video-based optical system for rapid measurements of chest wall movement," Physiol Meas 22, 489-503 (2001).

Zhang, Z., "A flexible new technique for camera calibration," IEEE Trans. on Pattern Analysis and Machine Intelligence, vol. 22(11), 1330-1334 (2000).

Poh et al., "Non-contact, automated cardiac pulse measurements using video imaging and blind source separation," Optics Express, vol. 18, No. 10, pp. 10762-10774, 2010.

Poh et al., "Advancements in non-contact, multiparameter physiological measurements using a webcam," IEEE Trans. on Biomedical Engineering, vol. 58, No. 1, Jan. 2011.

Rajapakse et al., "Approach and Applications of Constrained ICA," IEEE Trans. on Neural Networks, vol. 16, No. 1, Jan. 2005.

Moore, David, "A Real-World System for Human Motion Detection and Tracking", Final Thesis, California Institute of Technology, (2003).

Wang et al., "Intelligent Multimodal and Hyperspectral Sensing for Real-Time Moving Target Tracking", Applied Imagery Pattern Recognition Workshop (AIPR), pp. 1-8, (2008).

Al-Khalidi et al., "Tracking Human Face Features in Thermal Images for Respiration Monitoring", IEEE/ACS Int'l Conf. on Computer Systems and Applications (AICCSA), Hammamet, Tunisia, (May 16-19, 2010).

Fei et al., Analysis of Breathing Air Flow Patterns in Thermal Imaging, Proceedings of the 28th IEEE EMBS Annual International Conference, New York City, USA, pp. 946-952, (Aug. 30-Sep. 3, 2006).

Aoki et al., "Study on Respiration Monitoring Method Using Near-infrared Multiple Slit-lights Projection", IEEE International Symposium on Micro-NanoMechatronics and Human Science, pp. 291-296, (Nov. 7-9, 2005), ISBN: 0-7803-9482-8.

Eveland et al., "Tracking Human Faces in Infrared Video", Image and Vision Computing, vol. 21, pp. 579-590 (2003).

Aoki et al., Non-contact and Unrestrained Respiration Monitoring System for Sleeping Person Using Near-infrared Bright Spots Matrix Irradiation, IEEJ Transactions on Electronics, pp. 1251-1258, vol. 124, No. 6, (Sep. 2004).

Murthy et al., Non-Contact Monitoring of Breathing Function Using Infrared Imaging, pp. 1-17, Technical Report No. UH-CS-05-09, Apr. 9, 2005.

* cited by examiner

PROCESSING A VIDEO FOR TIDAL CHEST VOLUME ESTIMATION

CROSS REFERENCE TO RELATED APPLICATIONS

The present patent application is related to commonly owned and concurrently filed U.S. Pat. No. 8,971,985 entitled: "Minute Ventilation Estimation Based On Depth Maps", by Bernal et al., and U.S. patent application Ser. No. 13/416,715 entitled: "Minute Ventilation Estimation Based On Chest Volume", by Bernal et al., which are incorporated herein in its entirety by reference.

TECHNICAL FIELD

The present invention is directed to systems and methods for estimating tidal chest volume by analyzing distortions in reflections of structured illumination patterns captured in a video containing a partial view of a thoracic region of a subject of interest being monitored for respiratory function.

BACKGROUND

Monitoring respiratory events is of clinical importance in the early detection of potentially fatal conditions. Current technologies involve contact sensors the individual must wear constantly. Such a requirement can lead to patient discomfort, dependency, loss of dignity, and further may fail due to a variety of reasons including refusal to wear the monitoring device. Elderly patients and neo-natal infants are even more likely to suffer from the adverse effects of continued monitoring. Unobtrusive, non-contact, imaging based methods are increasingly needed for monitoring patient respiratory function.

Accordingly, what is needed in this art are sophisticated systems and methods for estimating tidal chest volume by analyzing distortions in reflections of structured illumination patterns captured in a video of a thoracic region of a subject of interest being monitored for respiratory function.

INCORPORATED REFERENCES

The following U.S. patents, U.S. patent applications, and Publications are incorporated herein in their entirety by reference.

"Processing A Video For Vascular Pattern Detection And Cardiac Function Analysis", U.S. Pat. No. 8,897,522.

"3D Imaging Using Structured Light For Accurate Vehicle Occupancy Determination", U.S. Pat. No. 9,007,438.

"Multi-Band Infrared Camera System Optimized For Skin Detection", U.S. patent application Ser. No. 13/416,436, by Wang et al.

"Monitoring Respiration With A Thermal Imaging System", U.S. Pat. No. 8,790,269.

"Web-Based System And Method For Video Analysis", U.S. Pat. No. 8,712,126.

"Filtering Source Video Data Via Independent Component Selection", U.S. Pat. No. 8,600,213.

"Removing Environment Factors From Signals Generated From Video Images Captured For Biomedical Measurements", U.S. patent application Ser. No. 13/401,207, by Mestha et al.

"*Structured-Light 3D Surface Imaging: A Tutorial*", by Jason Geng, Advances in Optics and Photonics Vol. 3, pp. 128-160, (Mar. 31, 2011) Optical Society of America.

"*Respiratory Physiology: The Essentials*", John B. West, Lippincott Williams & Wilkins; $9^{th}$ Ed. (2011), ISBN-13: 978-1609136406.

BRIEF SUMMARY

What is disclosed is a system and method for estimating tidal chest volume by analyzing distortions in reflections of structured illumination patterns captured in a video of a thoracic region of a subject of interest being monitored for respiratory function. Measurement readings can be acquired in a few seconds under a diverse set of lighting conditions and provide a non-contact approach to patient respiratory function monitoring that is particularly useful for infant care in a neo-natal intensive care unit (NICU), sleep studies, and can aid in the early detection of sudden deterioration of physiological conditions due to detectable changes in tidal chest volume. The systems and methods disclosed herein provide an effective tool for non-contact tidal chest volume estimation and respiratory function analysis.

One embodiment of the present method involves the following. First, a video is received of a thoracic region of a subject of interest being monitored for respiratory function. The target region can be, for instance, the subject's anterior thoracic region. The received video was captured using a video camera system and an illuminator configured to project a pattern of structured illumination. The video camera is sensitive to electromagnetic radiation in a wavelength range that overlaps with the wavelength of the projected structured illumination. Each of the captured images of the video comprises data of sampled radiation emitted by a reflection of the illumination source off the subject's target region. The spatial characteristics of the reflections captured by the images are then compared to known spatial characteristics of undistorted projected patterns such that spatial distortions of the captured patterns introduced by reflections of the pattern off the surface of the target region can be characterized. A depth map is calculated from the characterized spatial distortion. Tidal chest volume is estimated for the subject by estimating a volume at both inspiration and expiration and determining a difference between the two. Various embodiments are disclosed.

Many features and advantages of the above-described method will become readily apparent from the following detailed description and accompanying drawings.

BRIEF DESCRIPTION OF THE DRAWINGS

The foregoing and other features and advantages of the subject matter disclosed herein will be made apparent from the following detailed description taken in conjunction with the accompanying drawings, in which.

DETAILED DESCRIPTION

What is disclosed is a system and method for estimating tidal chest volume by analyzing distortions in reflections of structured illumination patterns captured in a video of a thoracic region of a subject of interest being monitored for respiratory function.

Non-Limiting Definitions

Figure 1:
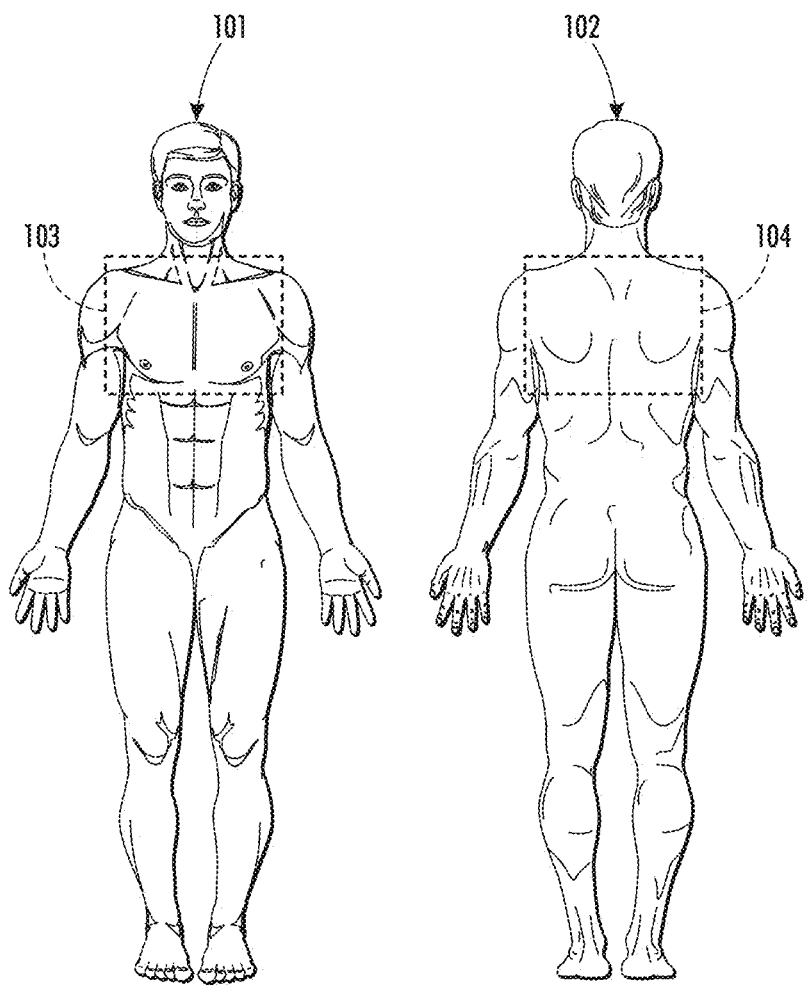
FIG. 1 shows both an anterior (frontal) view and a posterior (rear) view of an adult human.

A "subject of interest" refers to a subject being monitored for respiratory function such that a tidal chest volume can be determined in accordance with the teachings hereof. FIG. 1 shows an anterior (frontal) view 101 of an adult human as well as a posterior (rear) view 102. Target region 103 outlines the subject's anterior thoracic region. Target region 104 outlines the subject's posterior thoracic region. A target region, as used herein, also refers to any view of a region of the subject's body which performs a respiratory function from which tidal chest volume can be derived. It should be appreciated that the use of the terms "human", "person", or "patient" herein is not to be viewed as limiting the scope of the appended claims solely to human subjects of interest. The teachings hereof apply equally to other subjects of interest which also have a respiratory function. Such additional subjects include, for example, mammals, birds, fish, reptiles, and even certain insects.

A "respiratory function" is a multi-stage process involving inhaling air into the lungs (inspiration), gas exchange, and exhaling air out of the lungs (expiration) followed by a post-expiratory pause. Inhalation causes the lungs contained within the chest cavity to fill with air thereby expanding chest volume. Inhalation is initiated by a diaphragm muscle and supported intercostal muscles. Under normal conditions, the diaphragm is the primary driver of inhalation. When the diaphragm contracts, the rib cage expands and the contents of the abdomen are moved downward. This results in a larger thoracic volume and negative pressure (with respect to atmospheric pressure) inside the thorax. Gas exchange is a primary function of the respiratory system. Molecules of gases are exchanged between the external environment and a blood system. This exchange facilitates oxygenation of the blood and removal of carbon dioxide and other metabolic wastes from the body. Gas exchange also helps maintain the acid-base balance of the body. The cellular mechanism of gas exchange is carried out by the simple phenomenon of pressure difference. When the atmospheric pressure is low outside, air from the lungs flow out into the environment. When the air pressure is low inside the lungs, the opposite occurs.

Exhalation is generally a passive process due to the natural elasticity of lung tissue which causes them to recoil from the stretch of inhalation thus forcing air out until the pressures in the chest and the pressure of the outside atmosphere reach equilibrium. During forced exhalation, as when blowing out a candle, expiratory muscles including abdominal muscles and internal intercostal muscles, generate abdominal and thoracic pressure which helps force air out of the lungs. During forced inhalation, as when taking a deep breath, external intercostal muscles and accessory muscles aid in expanding the thoracic cavity and bringing more air into the lungs. During vigorous inhalation (at rates exceeding 35 breaths per minute), or in an approaching respiratory failure, accessory muscles such as the sternocleidomastoid, platysma, the scalene muscles of the neck as well as the pectoral muscles and latissimus dorsi of respiration are recruited for support. A post-expiratory pause occurs when there is an equalization of pressure between the lungs and the atmosphere. The duration of the post-expiratory pause reduces with increased physical activity and may even fall to zero at high rates of exertion. When the subject is at rest, the duration of the post-expiratory pause is relatively long. The subject's respiration cycle is the time interval between the beginning of inhalation and the end of the post-expiratory pause. Immediately following the post-expiratory pause is the start of the next cycle. The subject's respiration rate is the number of breaths a subject takes within a certain amount of time (typically in breaths/minute). Respiration rate is often measured when a subject is at rest and simply involves counting the number of breaths taken in a minute. A resting adult human takes about 12-20 breaths per minute depending on the overall condition of the cardio-vascular and respiratory systems.

Figure 2:
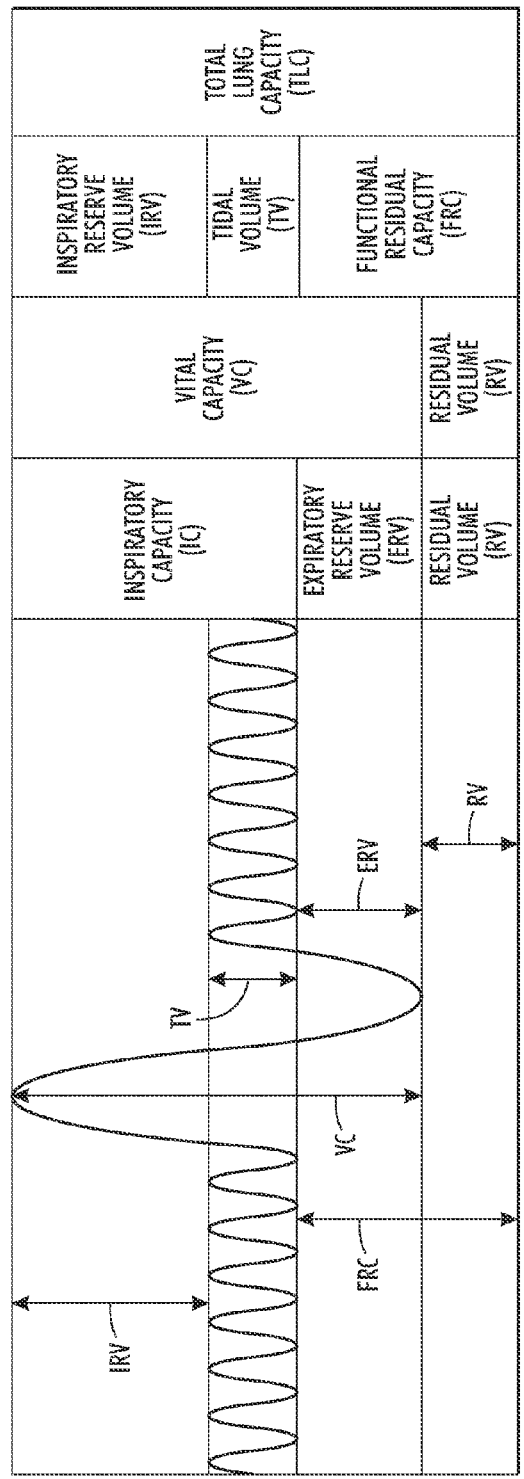
FIG. 2 plots the output of a spirometer of a normal person taking seven tidal breaths, followed by maximal inspiration and expiration.

"Chest volume" is the volume of air displaced by inspiration and expiration. Tidal breathing refers to normal breathing as opposed to heavy breathing due to exercise, for example. Thus, tidal chest volume or simply tidal volume (TV) is the volume of air drawn into the lungs during tidal breathing. In a healthy, young adult, tidal chest volume is about 0.5 Liters of air. Since total lung capacity of an average adult human is approximately 6.0 liters of air, the lungs displace a relatively small volume after inspiration and expiration while tidal breathing. Restrictive pulmonary diseases such as pulmonary fibrosis, pneumothorax, Infant Respiratory Distress Syndrome, and the like, decrease lung volume, whereas obstructive pulmonary diseases such asthma, bronchitis, and emphysema, obstruct airflow. FIG. 2 shows the output from a spirometer of a normal person taking seven tidal breaths, followed by maximal inspiration and expiration. TABLE 1 provides average volume values (in liters) for healthy adult human males and females

TABLE 1

| Volume | Average (in liters) | | Derivation |
| --- | --- | --- | --- |
| | In men | In women | |
| Tidal Volume (TV) | 0.5 | 0.5 | |
| Expiratory Reserve Volume (ERV) | 1.0 | 0.7 | |
| Residual Volume (RV) | 1.2 | 1.1 | |
| Inspiratory Reserve Volume (IRV) | 3.3 | 1.9 | |
| Vital Capacity (VC) | 4.6 | 3.1 | IRV + TV + ERV |
| Inspiratory Capacity (IC) | 3.8 | 2.4 | IRV + TV |
| Functional Residual Capacity (FRC) | 2.2 | 1.8 | ERV + RV |
| Total Lung Capacity (TLC) | 6.0 | 4.2 | IRV + TV + ERV + RV |

Expiratory Reserve Volume (ERV) is the maximal volume of air that can be exhaled from the end-expiratory position. Residual Volume (RV) is the volume of air remaining in the lungs after maximal exhalation (residual air remains in the lungs no matter how hard one tries to expel all their air). Inspiratory Reserve Volume (IRV) is the maximal volume of air that can be inhaled at the end-inspiratory level. Vital Capacity (VC) is the maximum amount of air a person can expel from the lungs after maximum inhalation. Inspiratory Capacity (IC) is the volume of air that can be inhaled after normal inspiration. Functional residual capacity (FRC) is the volume in the lungs at the end-expiratory position. Total Lung Capacity (TLC) is the total volume of air in the lungs at maximal inflation.

A "video", as is generally understood, is a time-varying sequence of image frames captured over time using a video camera. A fully populated 2D image captured using, for example, a 3-channel color video camera is a 2D array of pixels with each pixel in the array having color values collected for pixels from each of those channels. A fully populated 2D image captured using, for example, a single channel video camera is a 2D array of pixels with each pixel in the array having an intensity value measured for that pixel location at a desired wavelength band of interest. The video may also contain other components such as, audio, time reference signals, and the like. The size of the video data may get large for longer video sequences. The video may also be processed or pre-processed to compensate for non-uniform illumination due to a curvature of a surface of the skin, for motion induced blur due to body or surface motion, imaging blur, and slow illuminant variation. Motion in the video may be compensated for using, for example, a video-based 2D image or 3D surface stabilization techniques.

"Receiving a video" is intended to be widely construed and means to retrieve, receive, capture with a video camera, or otherwise obtain a video for processing for tidal chest volume estimation in accordance with the present method. The video can be received from a memory or internal storage of the video camera system, or obtained from a remote device over a network. The video may also be retrieved from a media such as a CDROM or DVD. The video may be received by being downloaded from a website which makes such videos available for pre-processing or post-processing. One such web-based system is disclosed in the above-incorporated US patent application entitled: "Web-Based System And Method For Video Analysis" by Piratla et al. The video can also be retrieved using an application such as those which are widely available for handheld cellular devices and processed on the user's cellphone or other handheld computing device such as an iPad.

Figure 3:
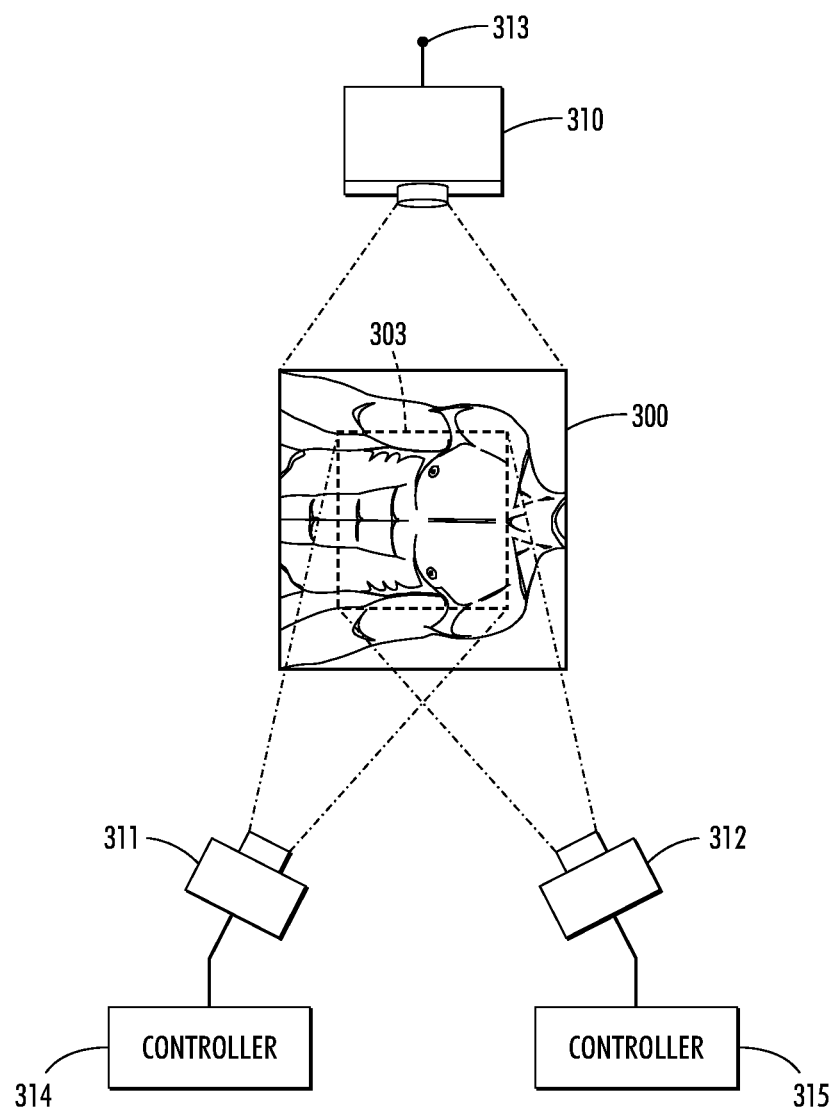
FIG. 3 illustrates an example scene illuminated with a structured light source and a video camera actively acquiring a video of a subject's chest area for tidal chest volume estimation in accordance with the teachings hereof.

A "video system" refers to a video camera for capturing a video and a structured illumination source which projects light through a patterned grid or window. The pattern may be a pseudo-random pattern with known spatial characteristics. Accurate 3D surface profiles of objects in a scene can be computed using structured-light principles and triangulation-based image reconstruction techniques. FIG. 3 shows a single 2D image frame 300 being captured of a target region 303 of the subject of interest of FIG. 1. Video camera 310 captures reflected energy off the target region emitted by structured illumination source 311. Illumination source 311 can be manipulated by varying the light source either spatially, temporally, spectrally, or any combination simultaneously. Video camera 310 is shown having a communication element 313 to effectuate a bi-directional communication with a remote device, such as a computer workstation, wherein the video is received for processing. A video imaging system may further comprise a video analysis module. Controllers 314 and 315 are shown to effectuate a manipulation of structured illumination source 311 and 312, respectively, to reduce artifacts. Methods for reducing such artifacts are disclosed in the above-incorporated reference: "*Enabling Hybrid Video Capture Of A Scene Illuminated With Unstructured And Structured Illumination Sources*", by Xu et al.

A "video analysis module", in one embodiment, comprises a hardware device such as an ASIC with at least one processor capable of executing machine readable program instructions for analyzing video images on a frame-by-frame basis for tidal chest volume determination. Such a module may also comprise, in whole or in part, a software application working alone or in conjunction with one or more hardware resources. Software applications may be executed by processors on different hardware platforms or emulated in a virtual environment. Aspects of the video analysis module may leverage off-the-shelf software.

A "remote sensing environment" refers to a non-contact, unobtrusive non-invasive means of acquiring data from a subject, i.e., the sensing device does not physically contact the subject being sensed. The sensing device can be any distance away from the subject, for example, as close as less than an inch to as far as miles in the case of telemedicine. The teachings hereof find their intended uses in such a remote sensing environment such that the resting cardiac patient remains undisturbed.

A "depth map" is a map containing depth values based upon an analysis of the amount of distortion of a structured light pattern reflected from surfaces in that region of the image. Once the depth map has been generated, a volume can be calculated.

3D Image Reconstruction

Figure 4:
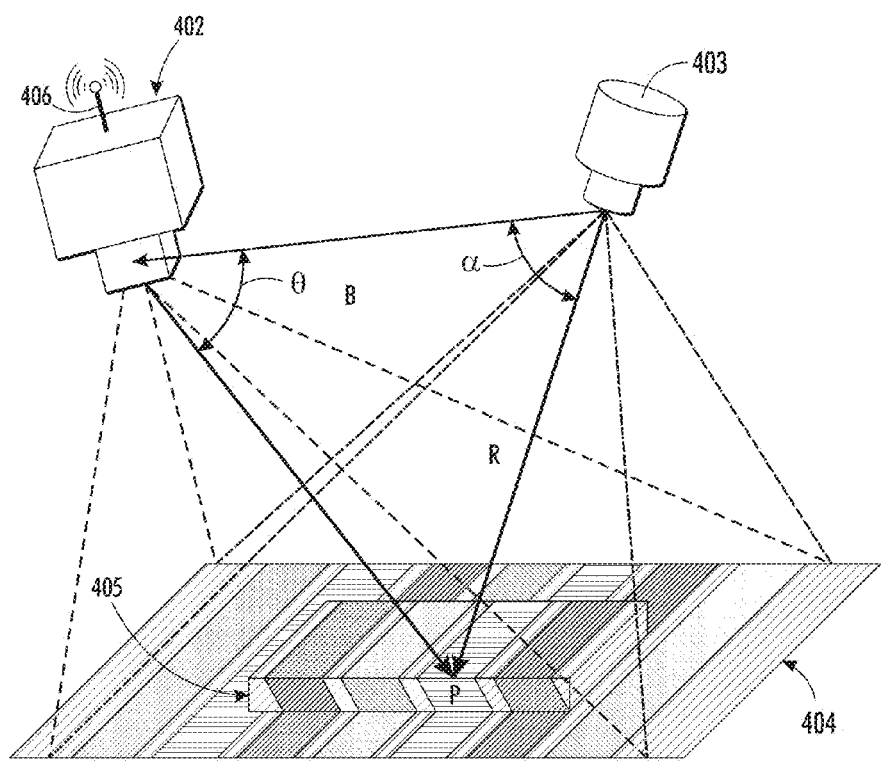
FIG. 4 shows the geometric relationships between an imaging sensor, a structured-light projector, and an object surface point expressed in terms of a triangulation.

In FIG. 4, structured illumination source 403 projects sinusoidal gratings 404 onto an object 405 and the reflection of the impinging sinusoidal gratings is captured by the camera system 402 as they bounce off the object. The sinusoidal gratings have known spatial characteristics of undistorted projected patterns. Camera system 402 is shown having a communication element 406 for bi-directional communication with a remote device, such as a workstation (not shown) wherein the captured video is communicated for processing. If the scene is a planar surface without any 3D surface variation and oriented approximately parallel to the camera sensor, the pattern shown in the acquired image will be similar to that of the projected structured-light pattern. However, when the surface is non-planar and contains a 3D object 405, the shape of the object distorts the projected structured light pattern. Such light distortions can be detected by camera 402. The geometric relationship between camera 402, a structured illumination source 403, and a point P on the surface of 3D object 405 can be expressed in terms of a triangulation as follows:

$$R = B \frac{\sin(\theta)}{\sin(\alpha + \theta)} \qquad (1)$$

Figure 5:
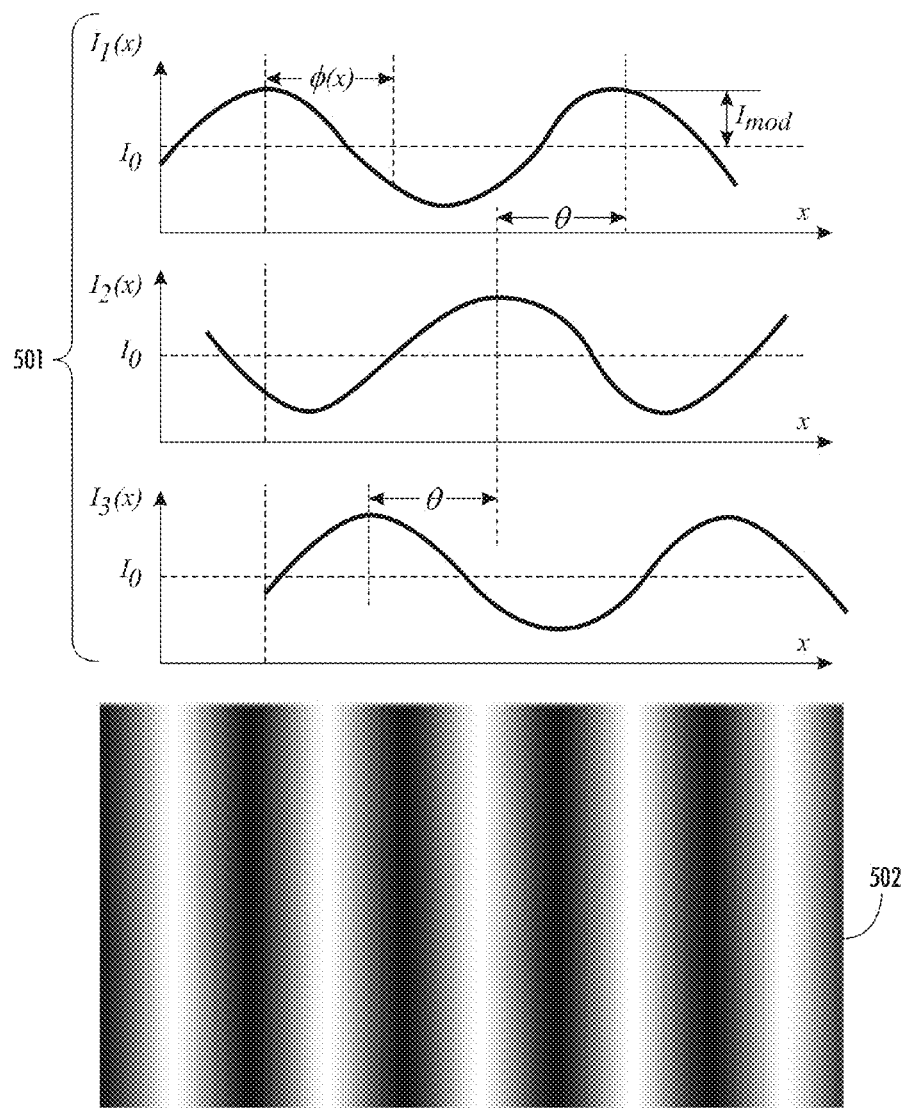
FIG. 5 shows the phase shift with three projection patterns and an example fringe image.

Accurate 3D image reconstruction can be based on a phase-shifting or phase modulation technique which measures phases at different locations on the object's surface and computes depth information from these phases. FIG. 5 shows the phase shift with three projection patterns, collectively at 501, projected onto the object surface, and an example fringe image 502. Phase shift is a well-known method wherein intensities for each pixel (x,y) of the three projected fringe patterns are described by the following relationships:

$$I_1(x,y)=I_0(x,y)+I_{mod}(x,y)\cos(\phi(x,y)-\theta), \quad (2)$$

$$I_2(x,y)=I_0(x,y)+I_{mod}(x,y)\cos(\phi(x,y)), \quad (3)$$

$$I_3(x,y)=I_0(x,y)+I_{mod}(x,y)\cos(\phi(x,y)+\theta), \quad (4)$$

where $I_1(x,y)$, $I_2(x,y)$ and $I_3(x,y)$ are the intensities of three fringe patterns, $I_0(x,y)$ is the DC component (background), $I_{mod}(x,y)$ is the modulation signal amplitude, $\phi(x,y)$ is the phase, and $\theta$ is the constant phase-shift angle.

Phase unwrapping is the process that converts the wrapped phase to the absolute phase. The phase information $\phi(x,y)$ can be retrieved (i.e., unwrapped) from the intensities in the three fringe patterns:

$$\phi' = \arctan\left[\sqrt{3}\,\frac{I_1(x,y)-I_3(x,y)}{2I_2(x,y)-I_1(x,y)-I_3(x,y)}\right] \quad (5)$$

Figure 6:
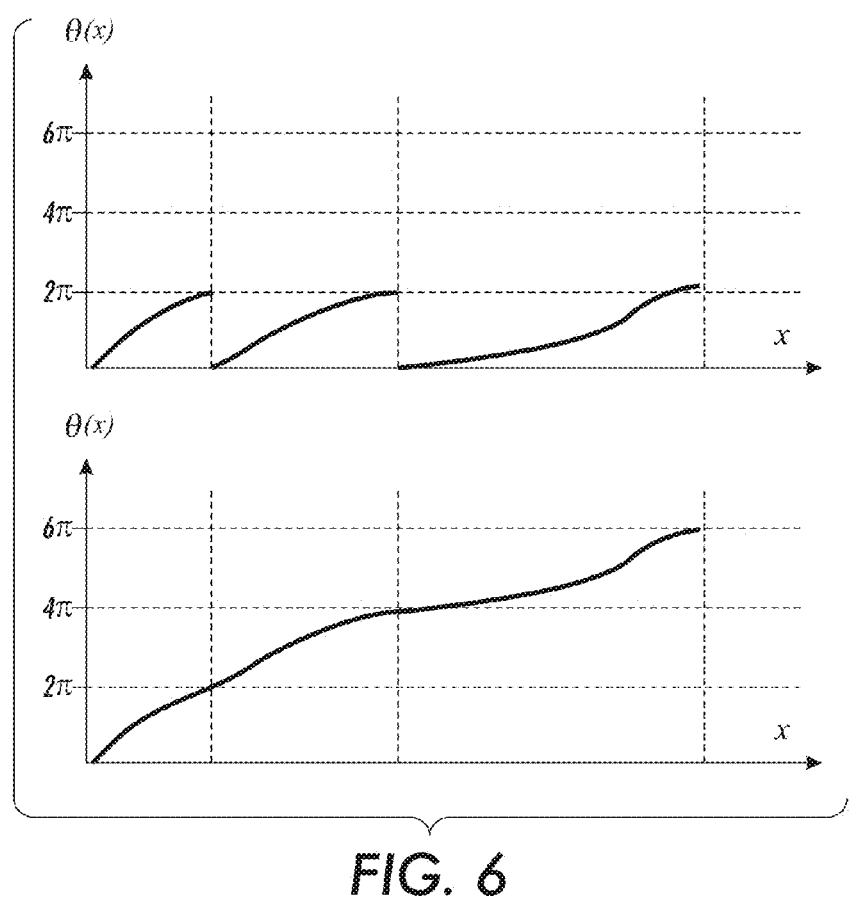
FIG. 6 illustrates one example embodiment of a phase unwrapping process.

The discontinuity of the arc tangent function at $2\pi$ can be removed by adding or subtracting multiples of $2\pi$ on the $\phi'(x,y)$ value (of FIG. 6):

$$\phi(x,y)=\phi'(x,y)+2k\pi \quad (6)$$

where k is an integer representing projection period. Note that unwrapping methods only provide a relative unwrapping and do not solve for the absolute phase. The 3D (x,y,z) coordinates can be calculated based on the difference between measured phase $\phi(x,y)$ and the phase value from a reference plane.

Figure 8:
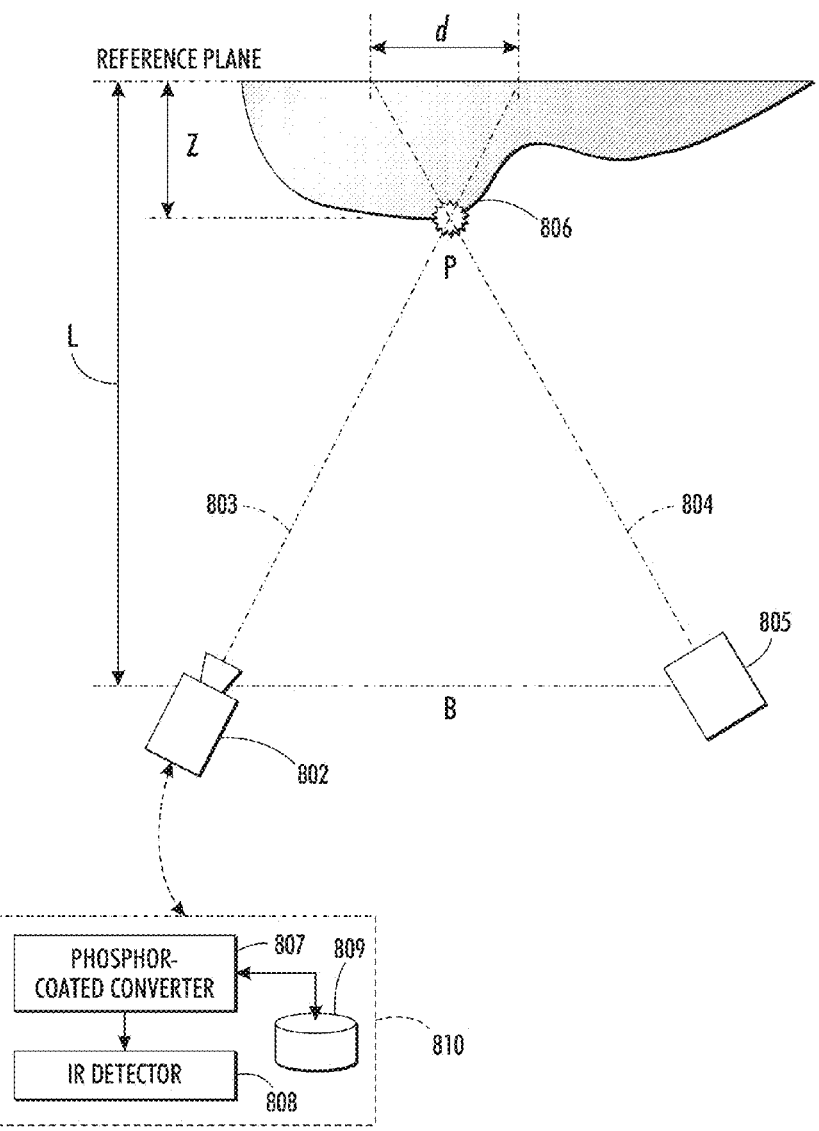
FIG. 8 shows a system which utilizes an image sensor to sense reflected light emitted by a patterned source projector in accordance with one embodiment hereof.

Reference is now being made to the system of FIG. 8 which utilizes a video camera 802 to sense reflected light emitted (at 804) by patterned illumination source projector 805 being reflected off point P of object 806, i.e., a location in the subject's thoracic region. Detector 808 generates pixel intensity values for pixel locations in the image. Pixel intensity values and wavelength data are provided to storage media 809. In FIG. 8, depth values are calculated by geometries given by:

$$\frac{Z}{L-Z} = \frac{d}{B} \quad (7)$$

which reduces to:

$$Z \approx \frac{L}{B}d \quad (8)$$

The camera and the illuminator form a stereo pair with a baseline distance b=7.5 cm. The projector sends out a fixed pattern of light and dark speckles. Since the spatial characteristics of the pattern are known and the pattern warps as the depth of the target surface changes, distances to the target can be estimated by determining the shape of the warping locally. Local correlation operations are performed between the captured and the stored pattern. The best match gives an offset from the known depth in pixels called disparity, d. The relationship between disparity and depth is given by:

$$Z = \frac{b*f}{d} \quad (9)$$

where z is the estimated depth in meters, f is the focal length of the camera in pixels, and b is the baseline distance.

Figure 7:
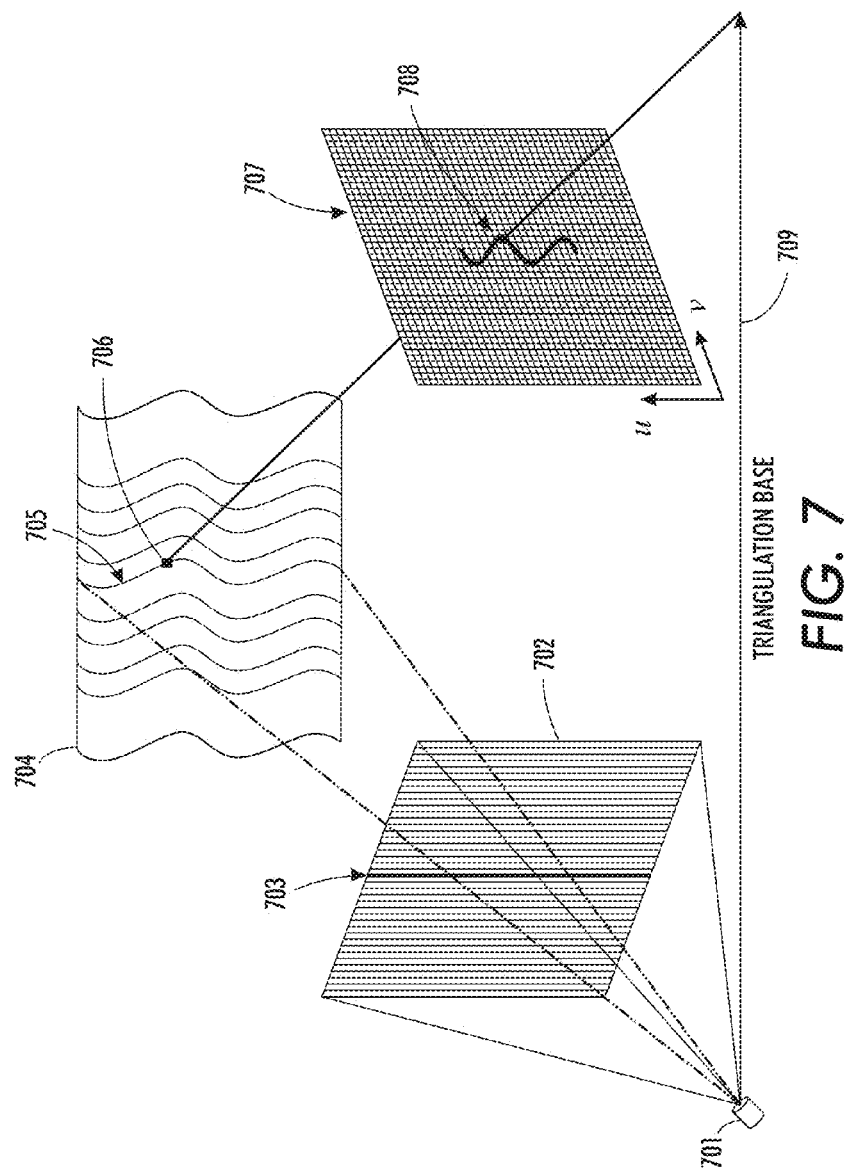
FIG. 7 shows an example stripe projection system.

Stripe indexing can also be used to achieve robust 3D surface reconstruction because the order in which the stripes are observed is not necessarily the same as the order in which the stripes are projected due to the inherent parallax existing in triangulation-based 3D surface imaging systems and the possibility to have stripes missing from the acquired image due to occlusion of 3D surface features. FIG. 7 shows an example stripe projection system wherein structured source light 701 is projected through stripped projector 702 with stripe 703 being illustrated for explanatory purposes. The pattern is projected onto object 704 whereon light stripe 705 illuminates the object at pixel location 706. Pixel element 708 of camera matrix 707 detects the reflected source light at this pixel location. The collection of pixels forms the image. Use of color for stripe indexing in the projection patterns helps alleviate the ambiguity problem faced by phase-shift or multiple-stripe techniques using monochromatic patterns. This type of system enables encoding of multiple patterns into a single color projection image with each pattern possessing a unique color value. In order to reduce the decoding error rate, one can select a color set in which each color has a maximum distance from any other color in the set. The maximum number of colors is limited to a distance between colors that generates a minimal crosstalk in the acquired images.

It should be appreciated that if the target 3D object is static and the application does not impose stringent constraints on the acquisition time, multiple-shot (sequential) techniques can be used and may often result in more reliable and accurate results. On the other hand, if the target is moving, single-shot techniques are used to acquire a snapshot 3D surface image of the 3D object at a particular time instance. Single-shot techniques can be classified into techniques using continuously varying structured-light patterns, those using 1D encoding schemes (strip indexing), and those using 2D encoding schemes (grid indexing). Each technique has its own advantages and disadvantages, depending on the specific applications. Some techniques can be combined. For further information on 3D imaging techniques, the reader is respectfully directed to the above-incorporated reference entitled: "Structured-Light 3D Surface Imaging: A Tutorial", by Jason Geng.

It should also be appreciated that the illumination sources can be manipulated, i.e., spatially and/or temporally, spectrally varied during capture of the video by the video camera. An illumination source can be varied spatially by, for instance, moving that illumination source such that the source light is projected onto certain regions in the scene from different angles. An illumination source can be varied temporally by, for instance, toggling the projection of the source light on/off according to a schedule or a desired periodicity. An illumination source can be varied spectrally by, for instance, modifying the wavelength band of the electromagnetic radiation so that it doesn't interfere with other illumination sources and/or video cameras in the system. A device controller can be configured to vary the intensity of the source light that an illumination source projects.

Calibration

In order to convert the device-dependent depth readouts (in bytes) to device-independent quantities (in inches or meters), a calibration needs to be performed. The calibration of the spatial coordinates of the device (from pixels to meters or inches) can be performed in a manner which is substantially similar to the way a traditional RGB camera is calibrated. For example, the reference: "*A Flexible New Technique For Camera Calibration*", Z. Zhang, IEEE Trans. On Pattern Analysis and Machine Intelligence, Vol. 22(11), 1330-1334, (2000), teaches a method to estimate a spatial calibration model with 11 unknown parameters. Calibration of the depth output requires knowledge of the geometric configuration of the stereo pair (illumination and imaging modules).

As discussed, both the spatial coordinates and the depth readouts from the 3D imaging sensor can be translated into device independent units of length (such as meters or inches). This, however, does not guarantee that the estimated volumes correspond to the volume being measured, given the fact that the changes in chest cage volume may not be identical to the changes in lung volume due to differences in elasticity between the two. Thus, additional calibration may be desirable. Assuming a linear relation between estimated and actual volume, a proportionality constant can be estimated via laboratory tests conducted for different breathing levels over a range required for the measurements. The actual volume can be measured using a spirometer. The slope of the linear regression line between the measurements of the spirometer and those obtained with the 3D imaging system would provide the calibration constant.

Segmentation

Before tidal chest volume is estimated, the region of the depth map corresponding to the subject's body is preferably segmented in the images. This can be achieved in a plurality of ways. For example, since the distance from the camera to the bed's surface is known, the location of the subject's body can be extracted by detecting pixels surrounded by the bed's surface and located closer to the camera than the bed itself. Another method is to perform localization and then region-grow the target area to include pixels with similar depth information. This produces a resulting binary mask. Chest cage localization can be performed by judicious application of morphological operations on the binary mask that results from the body segmentation stage. For example, morphological opening of the mask with an appropriate size structuring element will remove pixels corresponding to the extremities and head given their relative size with respect to the chest area. Another way is to apply morphological skeletonization to the mask and determine the branch points of the resulting skeleton. These branch points will be approximately located at the neck and shoulders, thus providing indication of the location of the subject's thoracic region.

Flow Diagram of One Example Embodiment

Figure 9:
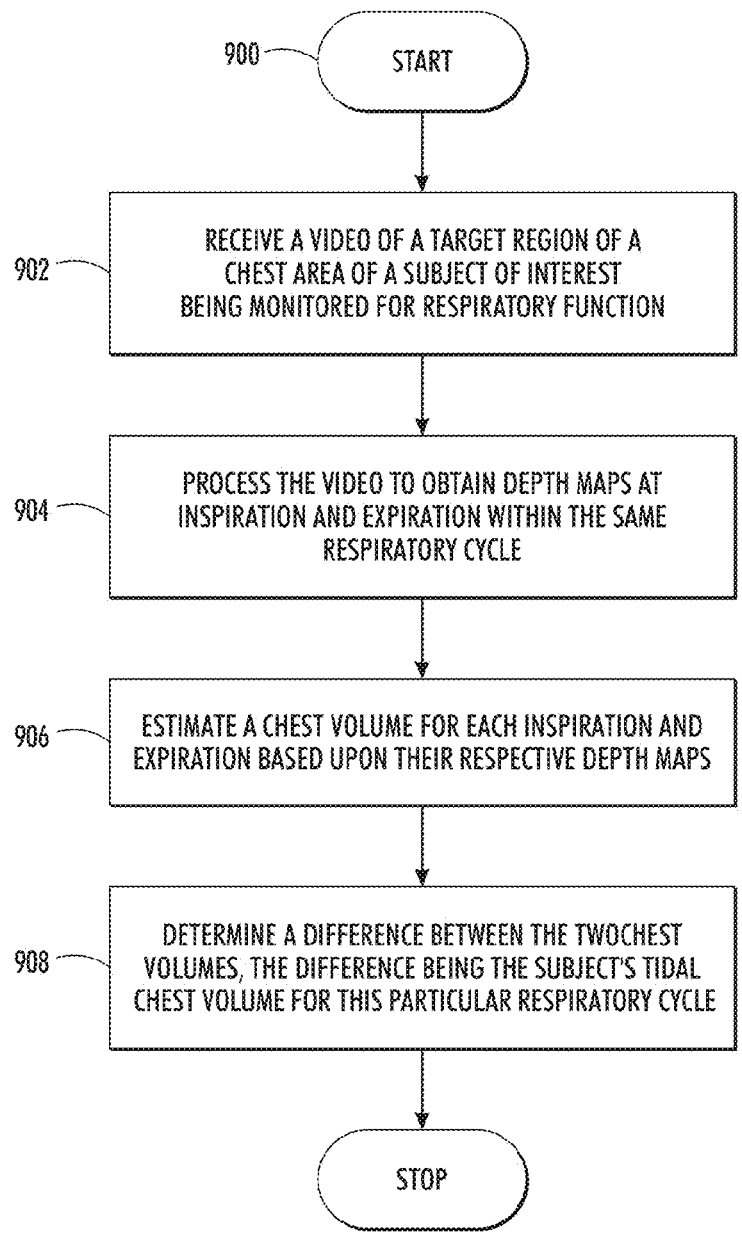
FIG. 9 is a flow diagram illustrating one example embodiment of the present method for estimating tidal chest volume from video captured of a subject of interest being monitored for respiratory function in a remote sensing environment.

Reference is now being made to the flow diagram of FIG. 9 which illustrates one example embodiment of the present method for estimating tidal chest volume from video captured of a subject of interest being monitored for respiratory function in a remote sensing environment. Flow processing begins at step 900 and immediately proceeds to step 902.

At step 902, receive a video of a target region of a chest area of a subject of interest being monitored for respiratory function. The video has been captured using a video camera and an illuminator configured to project a pattern of structured illumination. Example target regions of a subject of interest are shown and discussed with respect to the subject of interest of FIG. 1.

At step 904, compare the captured images to known spatial characteristics of undistorted patterns such that an amount of distortion of the captured patterns can be characterized.

At step 906, calculate a depth map from the characterized spatial distortions.

At step 908, estimate a 3D volume from the depth map. In one embodiment, tidal chest volume is estimated by tessellating surface points at various locations and computing a reference point location which, in various embodiments, comprises either a centroid, a weighted arithmetic mean, or a rank-ordered statistic of surface point locations. Tessellation is a technique for covering (or tiling) a surface with flat patterns (or surfaces) so that there are no overlaps and no gaps. Tetrahedrons are created by connecting triangles in the tessellation with the reference point. A tetrahedron is a polygon having four vertices with each face being formed by connecting three of the vertices to form a triangle. Three points of each triangle define a plane. There are four faces of a tetrahedron. A volume is computed for each tetrahedron. The total volume is the aggregate of all the tetrahedral volumes. This estimation is obtained after both inspiration and expiration. The difference between the two estimated volumes (after inspiration and expiration) is the total tidal chest volume for the subject.

Performance Results

Figure 10A:
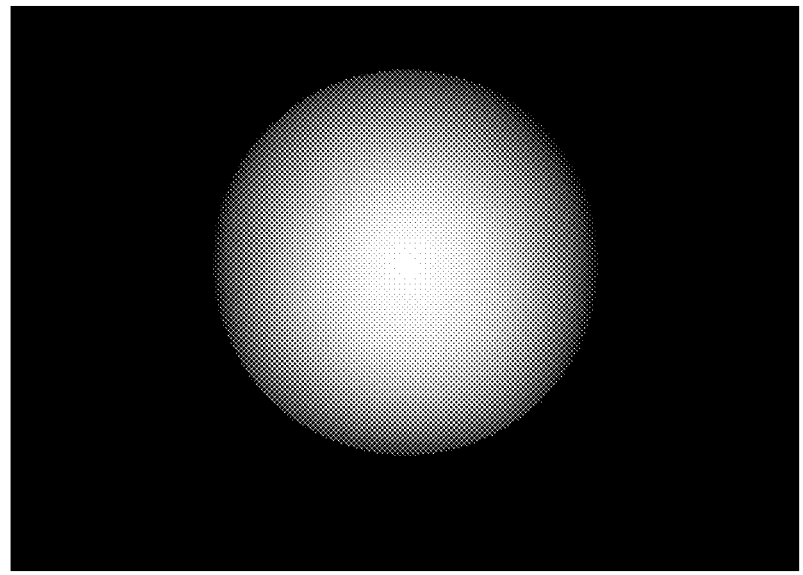
FIG. 10A shows a sample depth map of a sphere with a 15 mm radius constructed using a generic 3D image reconstruction algorithm.
Figure 10B:
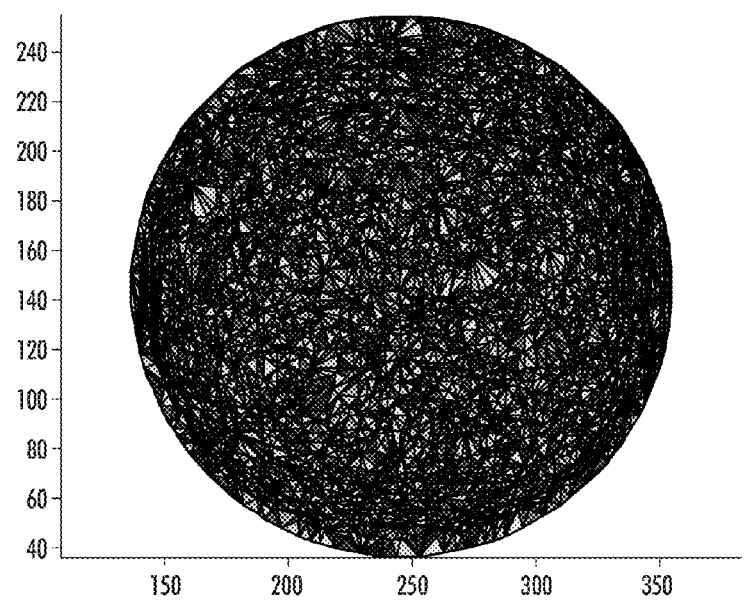
FIG. 10B shows the resulting 3D tessellation of the depth map of FIG. 10A.

FIG. 10A shows a sample depth map of a sphere reconstructed by a generic 3D imaging software. FIG. 10B shows the corresponding 3D tessellation. The radius of the sphere is 10.85 cm, so the actual volume is 5350 $cm^3$. The estimated 3D volume by aggregating the tetrahedral volumes was determined to be 4990 $cm^3$. This demonstrates that the teachings hereof provide an accurate estimation of the volume. The difference between the measured volumes will provide an estimate of tidal volume.

The volume estimation technique described herein was applied to the depth map created using pixels located in a chest area obtained from a video of a test subject during tidal breathing. Volumes of the chest cage of the test subject after inspiration and expiration were calculated with the methods described herein. For the test subject, the estimated tidal volume was 0.3 Liters. The average tidal volume in a healthy adult male is 0.5 Liters. The discrepancy between the numbers is due to factors such as the limited spatial and depth resolving resolution of the imaging system, and/or the fact that lung volume is not being measured directly (in other words, a change in the volume of the lungs does not translate into an identical change in the volume of the chest cage). In the latter case, a calibration table that describes the relationship between tidal chest volume and lung volume should be used to improve the accuracy of the estimation. In the present system, rather than volumes at specific time instances, continuous monitoring of the patient and continuous computation of tidal chest volume is preferable.

The flow diagrams depicted herein are illustrative. One or more of the operations illustrated in the flow diagrams may be performed in a differing order. Other operations may be added, modified, enhanced, or consolidated. Variations thereof are intended to fall within the scope of the appended claims.

Block Diagram of Video Processing System

Figure 11:
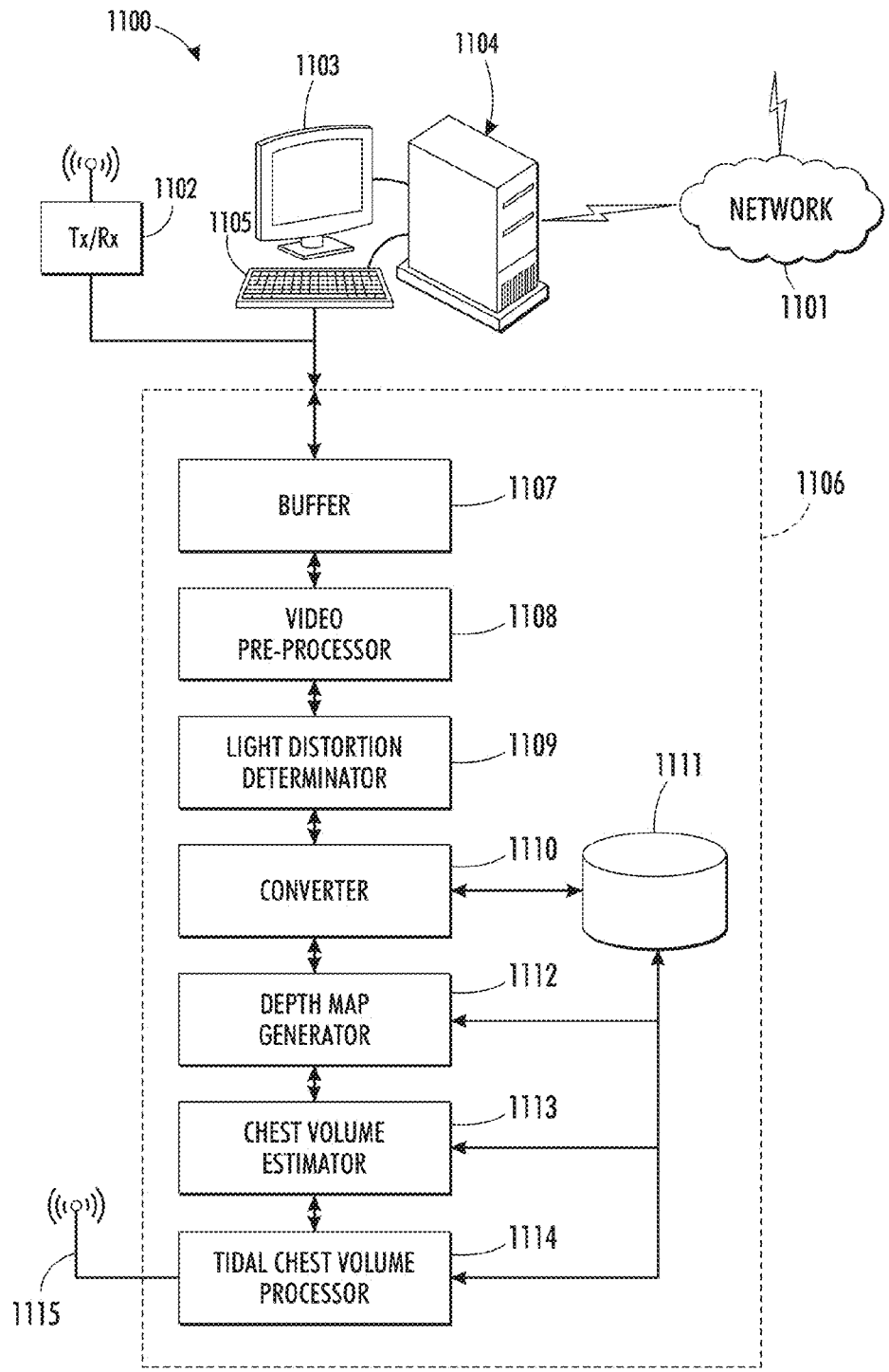
FIG. 11 illustrates a block diagram of one example video processing system for implementing various aspects of the present method as described with respect to the flow diagram of FIG. 9.

Reference is now being made to FIG. 11 which illustrates a block diagram of one example video processing system 1100 for implementing various aspects of the present method as described with respect to the flow diagram of FIG. 9.

In FIG. 11, workstation 1104 is placed in communication with communication element 1102 for receiving detected grid patterns from, for instance, video camera 303 of FIG. 3, and for otherwise effectuating communication between various devices and computer workstation 1104 via network 1101. Computer 1104 comprises monitor device 1103 and user interface 1105 for enabling a display of information for a user and for effectuating a user input or selection. An operator of the present system may use the graphical user interface 1103 to identify or otherwise select images of the captured video for processing or re-processing, and provide user input as may be required for the implementation hereof. Pixels and/or regions identified or otherwise detected in the received video may be retrieved from a remote device over network 1101. Various portions of the video may be stored to a memory or storage device 1111 in communication with workstation 1104 or may be communicated to a remote device over network 1101 via a communications interface (not shown) for remote storage or further processing. Workstation 1104 and communications interface 1102 are in communication with Image Processing Unit 1106 for processing the video in accordance with the teachings hereof.

Video Processing Unit 1106 is shown comprising a buffer 1107. Such a buffer may be used for queuing information about the received image such as, for instance, one or more target regions within the image frames, size of the video, time/date information, and the like. The buffer may be configured to also store data, mathematical formulas and other representations to facilitate processing of the image in accordance with the teachings hereof. Video Pre-Processor 1108 performs any pre-processing of the video as may be desired or required to compensate for non-uniform illumination due to a curvature of a surface of the skin, for motion induced blur due to body or surface motion, imaging blur, and slow illuminant variation. Processor 1108 may further be programmed to reduce the dimensionality of the data and performing Independent component analysis (ICA) on the video signal. Light Distortion Determinator 1109 determines an amount of distortion in the received pattern. The distortion is the determined amount of 3D surface variation. Depth Map Generator 1110 converts the determined amount of distortion to a depth value, on a pixel-by-pixel basis, for each image frame of the video and generates a depth map for each of the inspiration and expiration cycles of the subject. The depth map is then stored to storage device 1111. Information as required to perform any of the functions of any of the modules may be retrieved from storage device 1111 or may be received via a user input using the user interface of workstation 1104. Volume Estimation Processor Module 1113 retrieves the depth maps and proceeds to estimate a volume for each of the subject's inspiration and expiration cycles. As discussed herein, tidal chest volume estimation requires the computation of a difference between the volumes estimated at inspiration and expiration.

Processor 1113 is shown in communication with transmitter 1114 which is used to communicate the subject's estimated tidal chest volume to a third party such as, for example, the patient's physician, nurse, or respiratory therapist. Such a communication may take include some or all of the original video. Transmitted images may, in turn, be displayed on a graphical display device, such as that of workstation 1104, for visual review and further processing. The modules and processing units of FIG. 11 are in communication with monitor 1103 to present thereon information for a user selection. Any of the modules and/or processing units of FIG. 11 are in communication with storage device 1111 via pathways shown and not shown and may store/retrieve data, parameter values, functions, pages, records, and machine readable/executable program instructions required to perform their various functions. Each of the modules and processing units of the Video Processing System 1106 is also in communication with workstation 1104 via pathways not shown and may further be in communication with one or more remote devices over network 1101. It should be appreciated that some or all of the functionality for any of the modules may be performed, in whole or in part, by components internal to the workstation. It should also be appreciated that the workstation has an operating system and other specialized software configured to display a variety of numeric values, text, scroll bars, pull-down menus with user selectable options, and the like, for entering, selecting, or modifying information displayed on display device 1103.

Various modules of the embodiments hereof may designate one or more components which may, in turn, comprise software and/or hardware designed to perform the intended function. A plurality of modules may collectively perform a single function. Each module may have a specialized processor capable of executing machine readable program instructions. A module may comprise a single piece of hardware such as an ASIC, electronic circuit, or special purpose processor. A plurality of modules may be executed by either a single special purpose computer system or a plurality of special purpose computer systems in parallel. Connections between modules include both physical and logical connections. Modules may further include one or more software/hardware modules which may further comprise an operating system, drivers, device controllers, and other apparatuses some or all of which may be connected via a network. It is also contemplated that one or more aspects of the present method may be implemented on a dedicated computer system and may also be practiced in distributed computing environments where tasks are performed by remote devices that are linked through a network.

One or more aspects of the methods described herein are intended to be incorporated in an article of manufacture, including one or more computer program products, having computer usable or machine readable media. For purposes hereof, a computer usable or machine readable media is, for example, a floppy disk, a hard-drive, memory, CD-ROM, DVD, tape, cassette, or other digital or analog media, or the like, which is capable of having embodied thereon a computer readable program, one or more logical instructions, or other machine executable codes or commands that implement and facilitate the function, capability, and methodologies described herein. Furthermore, the article of manufacture may be included on at least one storage device readable by a machine architecture or image processing system embodying executable program instructions capable of performing the methodology described in the flow diagrams.

Various presently unforeseen or unanticipated alternatives, modifications, variations, or improvements therein may become apparent and/or subsequently made by those skilled in the art, which are also intended to be encompassed by the following claims. Accordingly, the embodiments set forth above are considered to be illustrative and not limiting. Various changes to the above-described embodiments may be made without departing from the spirit and scope of the invention. The teachings of any printed publications including patents and patent applications, are each separately hereby incorporated by reference in their entirety.

What is claimed is:

1. A method for determining chest volume from video captured of a subject of interest being monitored for respiratory function, the method comprising:

manipulating, in order to reduce image artifacts, at least one structured illumination source and at least one unstructured illumination source illuminating a scene being captured by a video system actively acquiring a video of a target region containing at least a partial view of a thoracic region of a subject of interest being monitored for respiratory function, captured images corresponding to at least an inspiration and expiration cycle of said subject, wherein said manipulating includes spectrally multiplexing said at least one structured illumination source and at least one unstructured illumination source by making a wavelength range of said at least one structured illumination source narrower than a wavelength range of said at least one unstructured illumination source such that reflected energy from both illumination sources can be recovered via filtering, said at least one structured illumination source and at least one unstructured illumination source having significantly overlapping spectral bands;

for each of said captured images, comparing spatial characteristics of said reflection in said captured images to known spatial characteristics of undistorted projected patterns such that a spatial distortion of captured patterns can be characterized, said spatial distortion having been introduced by a reflection of said captured patterns off a surface of said target region;

calculating a sequence of depth maps from said spatial distortion, in depth map being characterized for each of said captured images;

for each depth map in said sequence of depth maps:
  determining spatial coordinates corresponding to said depth map; and
  estimating a 3D chest volume for each depth map in said sequence of depth maps;

calculating said subject's chest volume using a proportionality constant which converts estimated 3D volumes to an approximation of a measured chest volume as measured by laboratory tests; and storing, using a processor, said subject's chest volume to a storage device.

2. The method of claim 1, wherein said target region comprises any of: an anterior thoracic region of said subject, a back region of said subject's dorsal body, and a side view of said thoracic region.

3. The method of claim 1, wherein estimating said 3D chest volume for each of said depth maps comprises:
  tessellating surface points of said depth map based on said determined spatial coordinates;
  computing a reference point location based on said determined spatial coordinates;
  connecting triangles in tessellation with said reference point to form tetrahedrons;
  computing a volume of each of said tetrahedrons; and
  aggregating tetrahedral volumes to obtain said estimated 3D chest volume for said depth map.

4. The method of claim 3, wherein said reference point location comprises one of:
  a centroid, a weighted arithmetic mean, and a rank-ordered statistic of surface point locations.

5. The method of claim 1, further comprising, in advance of estimating 3D volume, segmenting said depth map into regions corresponding to said subject's target region.

6. The method of claim 1, further comprising tracking a tidal chest volume over time to estimate any of: a respiration cycle and a respiration rate of said subject.

7. The method of claim 1, further comprising compensating for an effect of a body motion of said subject by any of: video-based image stabilization, and 3D surface stabilization.

8. The method of claim 1, wherein estimating said proportionality constant comprises:
  measuring said subject's lung volumes by a laboratory test over various stages of inspiration and expiration;
  performing linear regression between said measured lung volumes and said estimated 3D chest volumes; and
  calculating a slope of said linear regression to obtain said proportionality constant.

9. A system to determine chest volume from video captured of a subject of interest being monitored for respiratory function, the system comprising:
  a video camera and an illuminator configured to project a pattern of structured illumination, said video camera being, at least in part, sensitive to electromagnetic radiation in a wavelength range contains the wavelength of said structured illumination to capture time-varying video of a subject of interest being monitored for respiratory function; and
  a processor in communication with a memory, said processor executing machine readable instructions to perform:
    receive a video captured by said video camera of a target region containing at least a partial view of a thoracic region of said subject, each captured image comprising sampled radiation emitted by a reflection of a patterned structured illumination off said target region, said captured images corresponding to at least an inspiration and expiration cycle of said subject;
    manipulate, in order to reduce image artifacts, at least one structured illumination source and at least one unstructured illumination source illuminating a scene being captured by a video system actively acquiring a video of a target region containing at least a partial view of a thoracic region of a subject, said captured images corresponding to at least an inspiration and expiration cycle of said subject, wherein said manipulating includes spectrally multiplexing said at least one structured illumination source and at least one unstructured illumination source by making a wavelength range of said at least one structured illumination source narrower than a wavelength range of said at least one unstructured illumination source such that reflected energy from both illumination sources can be recovered via filtering, said at least one structured illumination source and at least one unstructured illumination source having significantly overlapping spectral bands;
    compare spatial characteristics of said reflection in said captured images to known spatial characteristics of undistorted projected patterns such that a spatial distortion of captured patterns can be characterized, said spatial distortion having been introduced by a reflection of said captured patterns off a surface of said target region;
    calculate a sequence of depth maps from said spatial distortion, in depth map being characterized for each of said captured images;
    for each depth map in said sequence of depth maps:
      determine spatial coordinates corresponding to said depth map; and
      estimate a 3D chest volume for each depth map in said sequence of depth maps;
    calculate said subject's chest volume using a proportionality constant which converts estimated 3D volumes to an approximation of a measured chest volume as measured by laboratory tests; and
    store said subject's chest volume to a storage device.

10. The system of claim 9, wherein said target region comprises any of: an anterior thoracic region of said subject, a back region of said subject's dorsal body, and a side view of said thoracic region.

11. The system of claim 9, wherein estimating said 3D chest volume for each of said depth maps comprises:
  tessellating surface points of said depth map based on said determined spatial coordinates;
  computing a reference point location based on said determined spatial coordinates;
  connecting triangles in tessellation with said reference point to form tetrahedrons;
  computing a volume of each of said tetrahedrons; and
  aggregating tetrahedral volumes to obtain said estimated 3D chest volume for said depth map.

12. The system of claim 11, wherein said reference point location comprises one of: a centroid, a weighted arithmetic mean, and a rank-ordered statistic of surface point locations.

13. The system of claim 9, further comprising, in advance of estimating said 3D volume, segmenting said depth map into regions corresponding to said subject's target region.

14. The system of claim 9, further comprising tracking a tidal chest volume over time to estimate any of: a respiration cycle and a respiration rate of said subject.

15. The system of claim 9, further comprising compensating for an effect of a body motion of said subject by any of: video image stabilization, and 3D surface stabilization.

16. A computer implemented method for determining chest volume from video captured of a subject of interest being monitored for respiratory function, the method comprising:
   manipulating, in order to reduce image artifacts, at least one structured illumination source and at least one unstructured illumination source illuminating a scene being captured by a video system actively acquiring a video of a target region containing at least a partial view of a thoracic region of a subject of interest being monitored for respiratory function, captured images corresponding to at least an inspiration and expiration cycle of said subject, wherein said manipulating includes spectrally multiplexing said illumination sources said at least one structured illumination source and at least one unstructured illumination source by making a wavelength range of said at least one structured illumination source narrower than a wavelength range of said at least one unstructured illumination source such that reflected energy from both illumination sources can be recovered via filtering, said at least one structured illumination source and at least one unstructured illumination source having significantly overlapping spectral bands;
   for each of said captured images, comparing spatial characteristics of said reflection in said captured images to known spatial characteristics of undistorted projected patterns such that a spatial distortion of captured patterns can be characterized, said spatial distortion having been introduced by a reflection of said captured patterns off a surface of said target region;
   calculating a sequence of depth maps from said spatial distortion, in depth map being characterized for each of said captured images;
   for each depth map in said sequence of depth maps:
      determining spatial coordinates corresponding to said depth map; and
      estimating a 3D chest volume for each depth map in said sequence of depth maps; and
   calculating said subject's chest volume using a proportionality constant which converts said estimated 3D volumes to an approximation of a measured chest volume as measured by laboratory tests.

17. The computer implemented method of claim 16, wherein estimating said 3D chest volume for each of said depth maps comprises:
   tessellating surface points of said depth map based on said determined spatial coordinates;
   computing a reference point location based on said determined spatial coordinates;
   connecting triangles in tessellation with said reference point to form tetrahedrons;
   computing a volume of each of said tetrahedrons; and
   aggregating tetrahedral volumes to obtain said estimated 3D chest volume for said depth map.

18. The computer implemented method of claim 16, further comprising tracking a tidal chest volume over time to estimate any of: a respiration cycle and a respiration rate of said subject.

19. The computer implemented method of claim 16, further comprising compensating for an effect of a body motion of said subject by any of: video image stabilization, and 3D surface stabilization.

* * * * *